United States Patent [19]

Mészáros et al.

[11] Patent Number: 4,666,912

[45] Date of Patent: May 19, 1987

[54] TREATING PROCESS

[75] Inventors: Zoltán Mészáros; József Knoll; István Hermecz, Péter Szentmiklósi; Ágnes Horváth; Lelle Vasvári née Debreczy; Gábor Kovács; Klára Gyires; Sándor Virág, all of Budapest, Hungary

[73] Assignee: Chinoin Gyogyszer es Vegyeszeti Termekek Gyara RT, Budapest, Hungary

[21] Appl. No.: 715,190

[22] Filed: Mar. 22, 1985

[30] Foreign Application Priority Data

Nov. 12, 1984 [HU] Hungary ............................. 4192/84

[51] Int. Cl.$^4$ .......................................... A61K 31/505
[52] U.S. Cl. ................................... 514/258; 514/926; 514/927
[58] Field of Search ...................... 514/258, 926, 927

[56] References Cited

FOREIGN PATENT DOCUMENTS 1583896 2/1981 United Kingdom .

OTHER PUBLICATIONS

Physicians' Desk Reference, 32nd Edition p. 1152 (1978).

Primary Examiner—Frederick E. Waddell
Attorney, Agent, or Firm—Karl F. Ross; Herbert Dubno

[57] ABSTRACT

The invention relates to a process for the restoration and prevention of gastrointestinal injuries, which comprises treating a patient with an effective dose of racemic or optically active 1,6-dimethyl-4-oxo-1,6,7,8,9,9a-hexahydro-4H-pyrimido[1,2-a]pyrimidine-3-carboxamide.

5 Claims, No Drawings

TREATING PROCESS

This invention relates to a process for preventing and treating gastrointestinal damage of humans and animals by administering racemic or optically active 1,6-dimethyl-4-oxo-1,6,7,8,9,9a-hexahydro-4H-pyrido(1,2-a)pyrimidine-3-carboxamide as active ingredient.

It is known that 1,6-dimethyl-4-oxo-1,6,7,8,9,9a-hexahydro-4H-pyrido(1,2-a)pyrimidine-3-carboxamide is of an analgetic and antiinflammatory activity (British patent specification No. 1,583,896; Arzneimittelforschung 29, 766 (1979)).

It is also known that serious damage and in severe cases even life-threatening gastrointestinal lesions are elicited by antiinflammatory agents (Trends in Pharm. Sci. 5, 156 (1984)).

The frequency of side effects of the most common and widely used antiinflammatory drugs are shown in Table 1.

These gastrointestinal lesions can only partly be treated with other drugs as the effects of these other drugs are only exerted in a restricted area of the gastrointestinal system (Burger's Medicinal Chemistry, 4th Ed. Vol. 2, pp. 835–853 and Vol. 3, pp. 361–406 and 507–534, John Wiley and Sons, 1979–1981).

Now, it has been found unexpectedly that a protection against or restoration of the damage caused by chemical or exogenous or endogenous agents was provided for the whole gastrointestinal system by a 10 to 1000 mg daily dose of 1,6-dimethyl-4-oxo-1,6,7,8,9,9a-hexahydro-4H-pyrido(1,2-a)pyrimidine-3-carboxamide.

The activity of the compound was investigated on the damage elicited: by indomethacin; by ethanol containing 2 ml of concentrated hydrochloric acid in 100 ml solution; and by 0.6 molar hydrochloric acid, respectively in male and female Sprague-Dawley CFY rats weighing 140 to 170 grams. Each group consisted of 10 animals. Before starting the experiment, the animals were acclimatized in a room at 21° C. for four days while they consumed food and water ad libitum. Twenty four hours before the experiment, the animals received only water.

The animals of the control group No. I. were orally given 20 mg/kg of body weight (in the following shortly: mg/kg) of indomethacin, or 0.5 ml of ethanolic hydrochloric acid, or 1 ml of 0.6 molar hydrochloric acid as ulcerating agent.

The animals of the control group No. II. received: subcutaneously 12.5 mk/kg of cimetidine at 30 minutes following indomethacin; or orally 50 mg/kg cimetidine at 40 minutes before giving the ethanolic hydrochloric acid; or orally 50 mg/kg of cimetidine at one hour before giving the 0.6 molar hydrochloric acid.

The animals of the control group No. III. received: subcutaneously 0.5 mg/kg atropine at 30 minutes following the oral dose of indomethacin; or subcutaneously 1.0 mg/kg of atropine at 20 minutes before giving the ethanolic hydrochloric acid; or subcutaneously 1.0 mg/kg of atropine at 30 minutes before giving the 0.6 molar hydrochloric acid.

The animals of the group IV. received: orally 50 mg/kg of 1,6-dimethyl-4-oxo-1,6,7,8,9,9a-hexahydro-4H-pyrido(1,2-a)pyrimidine-3-carboxamide simultaneously with indomethacin; or orally 50 mg/kg of 1,6-dimethyl-4-oxo-1,6,7,8,9,9a-hexahydro-4H-pyrido(1,2-a)pyrimidine-3-carboxamide at 40 minutes before giving the ethanolic hydrochloric acid; or orally 50 mg/kg of 1,6-dimethyl-4-oxo-1,6,7,8,9,9a-hexahydro-4H-pyrido(1,2-a)pyrimidine-3-carboxamide at one hour before administering the 0.6 molar hydrochloric acid.

The results were evaluated after the administration of the damaging agent, i.e. at 4 hours after indomethacin, at 2 hours after ethanolic hydrochloric acid and at one hour after 0.6 molar hydrochloric acid, respectively.

After decapitation, the stomach of the animals was opened along the great curvature and in the case of indomethacin, the injury of the gastric mucosa was determined by using Adami's method (Arch. Int. Pharmacodyn. 147, 113 (1964)). The alterations were classified according to the frequency and severity as follows:

| | |
|---|---|
| Intact mucosa | 0 |
| Punctiform hemorrhages | 1 |
| 1 to 5 small ulcers | 2 |
| Many small ulcers or 1 large one | 3 |
| Many large ulcers | 4 |

In the case of ethanolic hydrochloric acid and 0.6 molar hydrochloric acid, the alterations were evaluated according to the number, severity and frequency of the ulcers. The severity of ulcer formation was scored as follows:

| | |
|---|---|
| Intact mucosa | 0 |
| Ulcer or erosion of 1 to 2 mm in length | 1 |
| Ulcer of 2 to 3 mm in length | 2 |
| Ulcer of 3 to 4 mm in length | 3 |
| Ulcer longer than 4 mm | 4 |
| Thick ulcer longer than 4 mm | 5 |

The results shown in Table II. illustrate that 1,6-dimethyl-4-oxo-1,6,7,8,9,9a-hexahydro-4H-pyrido(1,2-a)pyrimidine-3-carboxamide proved to be effective against all the three ulcerogenic agents, while cimetidine and atropine inhibited the formation of the indomethacine ulcer only.

1,6-Dimethyl-4-oxo-1,6,7,8,9,9a-hexahydro-4-pyrido(1,2-a)pyrimidine-3-carboxamide proved to be effective not only in an acute treatment as illustrated by the experimental results shown in Table III.

The arrangement of these experiments was similar to that of the acute experiments, with the exception that 1,6-dimethyl-4-oxo-1,6,7,8,9,9a-hexahydro-4-pyrido(1,2-a)pyrimidine-3-carboxamide was administered in an oral dose of 50 mg/kg for 4 consecutive days. The damaging agent (ethanolic hydrochloric acid or 0.6 molar hydrochloric acid) was administered on the fourth day and the experiment was evaluated similarly as described for the acute experiments.

1,6-Dimethyl-4-oxo-1,6,7,8,9,9a-hexahydro-4H-pyrido(1,2-a)pyrimidine-3-carboxamide was capable to provide a protective effect against the development of more severe alterations caused by either ethanolic hydrochloric acid or 0.6 molar hydrochloric acid.

Both the number and severity as well as the frequency of ulcers were diminished. Ulceration occurred in each animal of the control groups, while a less severe alteration in the stomach was observed in only 60% or 80%, respectively of the animals treated with 1,6-dimethyl-4-oxo-1,6,7,8,9,9a-hexahydro-4H-pyrido(1,2-a)pyrimidine-3-carboxamide.

A protective action or restoration of the developed injury, respectively was provided by 1,6-dimethyl-4- oxo-1,6,7,8,9,9a-hexahydro-4H-pyrido(1,2-a)pyrimidine-3-carboxamide not only in the stomach but in other segments of the gastrointestinal system as well. The effect on the ulcer formation in the intestine was investigated in a group of 10 Sprague-Dawley CFY rats in comparison with cimetidine and atropine. It is very important to recognize if a compound, inhibiting the injury of the gastric mucosa, could be capable to inhibit the ulceration of the intestine, too; when the injury of the gastric mucosa is only inhibited, then the intestinal ulcers may perforate (British J. Pharm. 67, 33 (1979)).

Similarly to the experiments described above, indomethacin was employed as the damaging agent.

The compound under investigation (cimetidine, atropine or 1,6-dimethyl-4-oxo-1,6,7,8,9,9a-hexahydro-4H-pyrido(1,2-a)pyrimidine-3-carboxamide, respectively) was administered to the animals on four consecutive days, while the damaging agent (indomethacin) was given once on the second day. During the experiment, the animals received food and water ad libitum. After the fourth day, the animals were killed, their abdomen was opened and the injuries of the gastrointestinal system were determined by using Tsumori's method (J. Pharm. D. 3, 659–660 (1980)). The ulcers were scored by the ulcus index as follows:

| Intact mucosa | 0 |
| 1 to 3 smaller ulcers or erosions | 1 |
| 1 to 5 ulcers or erosions | 2 |
| More than 5 ulcers or 1 to 3 perforated ulcers | 3 |
| Many perforated ulcers | 4 |

In addition to the observation of the dead animals and of the length of the small intestine from the pylorus to the coecum, the body weight of the animals and the frequency of ascites were also determined.

The control group No. I. did not receive any protective or damaging agent. The control group No. II. received only the damaging agent, i.e. indomethacin. The control group No. III. received the damaging agent and cimetidine, while the control group No. IV. was given atropine in addition to the damaging agent. The control group No. V. received 1,6-dimethyl-4-oxo-1,6,7,8,9,9a-hexahydro-4H-pyrido(1,2-a)pyrimidine-3-carboxamide for four days.

The group No. VI. received in addition to the damaging agent 1,6-dimethyl-4-oxo-1,6,7,8,9,9a-hexahydro-4H-pyrido(1,2-a)pyrimidine-3-carboxamide for four days. The results of these investigations are summarized in Table IV. It can be concluded that 1,6-dimethyl-4-oxo-1,6,7,8,9,9a-hexahydro-4H-pyrido(1,2-a)pyrimidine-3-carboxamide could only provide a protective effect concerning all parameters examined. The protective effect of atropine was much less pronounced.

Further on, the protective action of 1,6-dimethyl-4-oxo-1,6,7,8,9,9a-hexahydro-4H-pyrido(1,2-a)pyrimidine-3-carboxamide was investigated on the gastric ulcer formation elicited by absolute ethanol containing no hydrochloric acid in an acute and in a 4-day experiment. The results are shown in Table V.

In the acute experiment, 1,6,-dimethyl-4-oxo-1,6,7,8,9,9a-hexahydro-4H-pyrido(1,2-a)pyrimidine-3-carboxamide was orally administered to Sprague-Dawley CFY rats at 40 minutes before the oral administration of 0.5 ml of ethanol. In the course of the experiment lasting four days, the animals received orally 1,6-dimethyl-4-oxo-1,6,7,8,9,9a-hexahydro-4H-pyrido(1,2-a)pyrimidine-3-carboxamide on four consecutive days and on the fourth day, each of the animals was orally given 0.5 ml of ethanol at 40 minutes following 1,6-dimethyl-4-oxo-1,6,7,8,9,9a-hexahydro-4H-pyrido(1,2-a)pyrimidine-3-carboxamide. The ulcer-inhibiting activity was determined in both experimental arrangements at two hours after administering the damaging agent. The severity of ulcer formation was scored as follows:

| Intact mucosa | 0 |
| Ulcer or erosion of 1 to 2 mm in length | 1 |
| Ulcer of 2 to 3 mm in length | 2 |
| Ulcer of 3 to 4 mm in length | 3 |
| Ulcer longer than 4 mm | 4 |
| Thick ulcer longer than 4 mm | 5 |

As it is shown in Table V., 1,6-dimethyl-4-oxo-1,6,7,8,9,9a-hexahydro-4H-pyrido(1,2-a)pyrimidine-3-carboxamide inhibited the ulcer formation in the stomach in both an acute experiment as well as in the course of a 4-day treatment with ethanol.

On summarizing the Tables II. to V., it is obvious that 1,6-dimethyl-4-oxo-1,6,7,8,9,9a-hexahydro-4H-pyrido(1,2-a)pyrimidine-3-carboxamide was the single agent to exert a protective and preventive effect on the whole gastrointestinal system, while the effect of both cimetidine and atropine used as controls only concerned the protection of the stomach as depending on the damaging agent.

Thus, 1,6-diemthyl-4-oxo-1,6,7,8,9,9a-hexahydro-4H-pyrido(1,2-a)pyrimidine-3-carboxamide provides a protective action or restoration, respectively for the whole gastrointestinal system against the injuries caused by chemical or other exogenous and endogenous agents by using either preventive or curative treatment.

The treatment is carried out by the means of commonly used pharmaceutical compositions, such as tablets, capsules, dragées, suppositories and injections containing about 10 to 1000 milligrams of the active ingredient depending on the nature of formulation.

The use of once-a-day or divided doses may vary depending on the status and age of the patient, on the severity of the injuries and on the mode of application.

The oral daily dose may vary between 100 and 1000 mg.

Depending on the severity of the injuries developed a parenteral, particularly subcutaneous, intracutaneous or intravenous medication may also be used.

The daily intravenous dose may vary between 10 and 400 mg. On the subcutaneous administration, doses from 20 to 800 mg may be given.

The process of invention is illustrated in detail by the following non-limiting Examples.

TABLE I

Frequency of the gastrointestinal side effects of antiinflammatory drugs

| Drug | Frequency of ulcer formation in the stomach | Frequency of other injuries in the gastrointestinal system |
| --- | --- | --- |
| Acetylsalicylic acid | +++ | ++++ |
| Benoxaprofen | + | ++ |
| Fenoprofen | +++ | ++++ |
| Ibuprofen | ++ | +++ |
| Flufenamic acid | ++ | +++ |
| Indomethacin | +++ | ++++ |
| Ketoprofen | ++ | +++ |
| Naproxen | + | ++ |
| Phenylbutazone | + | ++++ |

TABLE I-continued

Frequency of the gastrointestinal side effects of antiinflammatory drugs

| Drug | Frequency of ulcer formation in the stomach | Frequency of other injuries in the gastrointestinal system |
|---|---|---|
| Piroxicam | +++ | ++++ |
| Sulindac | + | +++ |

+: the injury occurs in 0.1 to 5.0% of the cases
++: the injury occurs in 5.0 to 10.0% of the cases
+++: the injury occurs in 10.0 to 15.0% of the cases
++++: the injury occurs in more than 20.0% of the cases Chemical composition of the above antiinflammatory
drugs: Acetylsalicylic acid: 2-acetoxybenzoic acid
Benoxaprofen: 2-(4-chlorophenyl)-α-methyl-5-benzoxazole-acetic acid
Fenoprofen: 2-(3-phenoxyphenyl)-propionic acid
Flufenamic acid: 2-(3-trifluoromethylphenyl)-aminobenzoic acid
Ibuprofen: 2-[4-(2-methylpropyl)-phenyl]-propionic acid
Indomethacin: 1-[4-chlorobenzoyl]-2-methyl-5-methoxy-1H—indole-3-acetic acid
Ketoprofen: 2-(3-benzoylphenyl)-propionic acid
Naproxen: (+)-2-(6-methoxy-naphthyl)-propionic acid
Phenylbutazone: 1,2-diphenyl-4-butyl-3,4-dioxopyrazolidine
Piroxicam: N—(2-pyridinyl)-2-methyl-4-hydroxy-2H—1,2-banzothiazine-3-carboxamide-1,1-dioxide
Sulindac: 1-(4-methylsulphinylphenyl-methylene)-1H—indene-3-acetic acid

TABLE II

Comparison of the gastric ulceration-inhibiting effect of 1,6-dimethyl-4-oxo-1,6,7,8,9,9a-hexahydro-4H—pyrido[1,2-a]pyrimidine-3-carboxamide, cimetidine and atropine against various damaging agents

| Animal groups | Severity of the injury elicited by 20 mg/kg of indomethacin | Ulcer formation elicited by 0.5 ml of ethanolic hydrochloric acid | | | Ulcer formation elicited by 1 ml of 0.6 ml molar hydrochloric acid | | |
|---|---|---|---|---|---|---|---|
| | | Severity | Number | Frequency % | Severity | Number | Frequency % |
| Control I. (methylcellosolve 10 ml/kg) | 3.2 | 3.8 | 7.8 | 100 | 3.7 | 4.6 | 100 |
| Control II. 12.5 mg/kg of cimetidine s.c. or 50 mg/kg of cimetidine p.o. | 1.2 | 3.4 | 6.2 | 100 | 3.5 | 6.2 | 100 |
| Control III. 0.5 mg/kg of atropine s.c. or 1.0 mg/kg of atropine s.c. | 0.8 | 3.2 | 5.8 | 100 | 4.2 | 7.8 | 100 |
| Group IV. 1,6-dimethyl-4-oxo-1,6,7,8,9,9a-hexahydro-4H—pyrido[1,2-a]pyrimidine-3-carboxamide 50 mg/kg p.o. | 1.5 | 2.6 | 4.6 | 80 | 2.8 | 3.2 | 60 |

TABLE III

Protective action of 1,6-dimethyl-4-oxo-1,6,7,8,9,9a-hexahydro-4H—pyrido[1,2-a]pyrimidine-3-carboxamide against the gastric ulcer formation elicited by ethanolic or 0.6 molar hydrochloric acid within a treatment lasting four days

| Test compound | Ulcer formation elicited by 0.5 ml of ethanolic hydrochloric acid | | | Ulcer formation elicited by 0.6 molar hydrochloric acid | | |
|---|---|---|---|---|---|---|
| | Severity | Number | Frequency % | Severity | Number | Frequency % |
| Control I. (methylcellosolve 10 ml/kg) | 3.5 | 6.2 | 100 | 4.2 | 6.6 | 100 |
| 1,6-Dimethyl-4-oxo-1,6,7,8,9,9a-hexahydro-4H—pyrido[1,2-a]-pyrimidine-3-carboxamide 4 × 50 mg/kg p.o | 2.7 | 5.6 | 60 | 2.1 | 3.4 | 80 |

TABLE IV

Protective action of cimetidine, atropine or 1,6-dimethyl-4-oxo-1,6,7,8,9,9a-hexahydro-4H—pyrido-[1,2-a]pyrimidine-3-carboxamide, respectively on the intestinal ulcer elicited by indomethacin

| Animal group | Dose mg/kg | Perishment % | Frequency of ulcer formation % | Ulcer index (score) | Intestinal length cm | Body weight alteration (g) decreases (−) increase (+) | Frequency of ascites % |
|---|---|---|---|---|---|---|---|
| Control I. (methylcellosolve 10 ml/kg) | — | 0 | 0 | 0 | 118.8 | (+)9.1 | 0 |
| Control II. Indomethacin p.o. | 15 | 30 | 100 | 3.4 | 80.7 | (−)18.1 | 80 |
| Control III. Indomethacin p.o. + cimetidine s.c. | 15 4 × 25 | 20 | 100 | 3.35 | 76 | (−)16.5 | 90 |
| Control IV. Indomethacin p.o. + atropine s.c. | 15 4 × 25 | 15 | 70 | 2.1 | 100 | (−)8 | 50 |
| Control V. 1,6-Dimethyl-4-oxo-1,6,7,8,9,9a-hexahydro-4H—pyrido[1,2-a]pyrimidine-3-carboxamide p.o. | 4 × 50 | 0 | 0 | 0 | 119.2 | (+)8.5 | 0 |
| Group VI. Indomethacin p.o. + 1,6-dimethyl-4-oxo-1,6,7,8,9,9a-hexahydro[1,2-a]pyrimidine-3-carboxamide p.o. | 15 4 × 50 | 10 | 56 | 1.6 | 101.0 | (−)6.7 | 26 |

TABLE V

Protective action 1,6-dimethyl-4-oxo-1,6,7,8,9,9a-hexahydro-4H—pryridol 1,2-a/pyrimidine-3-carboxamide against the gastric ulcer formation elicited by ethanol in an acute experiment and within a treatment lasting four days

| Experiment | Dose mg/kg | Ulcer formation elicited by 0.5 ml of ethanol | |
|---|---|---|---|
| | | Severity | Frequency % |
| Acute: Control I. (methylcellosolve 10 ml/kg) | — | 1.8 | 80 |
| Acute: Group II. 1,6-Dimethyl-4-oxo-1,6,7,8,9,9a-hexahydro-4H—pyrido[1,2-a]pyrimidine-3-carboxamide p.o. | 50 75 | 0.8 0 | 40 0 |
| 4-day treatment: Control III. (methylcellosolve 10 ml/kg) | — | 26 | 90 |
| 4-day treatment: Group IV. 1,6-Dimethyl-4-oxo-1,6,7,8,9,9a-hexahydro-4H—pyrido[1,2-a]pyrimidine-3-carboxamide p.o. | 4 × 50 4 × 75 | 0.8 0 | 45 0 |

EXAMPLE 1

Preparation of tablets each containing 100 mg of the active ingredient

A mixture containing 1000 g of 1,6-dimethyl-4-oxo-1,6,7,8,9,9a-hexahydro-4H-pyrido(1,2-a)pyrimidine-3-carboxamide and 300 g of lactose was sieved, homogenized, then this powder mixture was moistened with 200 ml of a 5% aqueous gelatine solution. After drying and re-granulating, the granulate was homogenized with a powder mixture containing 20 g of magnesium stearate, 40 g of talc and 40 g of potato starch and compressed into tablets.

EXAMPLE 2

Preparation of tablets each containing 200 mg of the active ingredient

A mixture containing 2000 g of 1,6-dimethyl-4-oxo-1,6,7,8,9,9a-hexahydro-4H-pyrido(1,2-a)pyrimidine-3-carboxamide and 600 g of potato starch was seived, homogenized, then this powder mixture was moistened with 300 ml of a 5% aqueous solution. After drying and re-granulating, the granulate was homogenized with a powder mixture containing 40 g of talc, 30 g of magnesium stearate and 30 g of potato starch and compressed into tablets.

EXAMPLE 3

Preparation of tablets each containing 300 mg of the active ingredient

A mixture containing 3000 g of 1,6-dimethyl-4-oxo-1,6,7,8,9,9a-hexahydro-4H-pyrido(1,2-a)pyrimidine and 300 g of potato starch was sieved, homogenized, then this powder mixture was moistened with 500 ml of 5% aqueous gelatine solution. After drying and re-granulating, the granulate was homogenized with a powder mixture containing 120 g of talc, 50 g of magnesium stearate and 30 g of potato starch and compressed into tablets.

EXAMPLE 4

Preparation of dragées each containing 100 mg, 200 mg or 300 mg, respectively of the active ingredient A pigment suspension was employed for coating tablets containing 100 mg, 200 mg or 300 mg, respectively of 1,6-dimethyl-4-oxo-1,6,7,8,9,9a-hexahydro-4H-pyrido(1,2-a)pyrimidine-3-carboxamide.

A finely powdered mixture containing 64 g of talc and 50 g of titanium dioxide was homogenized with 268 g of isopropanol. A colored aqueous solution was prepared containing 4 g of a water-soluble dye and 6 g of Carbowax 6000 in 12 g of water and mixed with the above-prepared suspension. The thus obtained varnish suspension was applied for coating the surface of 1000 tablets.

EXAMPLE 5

Preparation of an injection solution (2 ml/100 g)

1000 g of 1,6-dimethyl-4-oxo-1,6,7,8,9,9a-hexahydro-4H-pyrido(1,2-a)-pyrimidine-3-carboxamide were weighed in a volumetric flask of 2 liters volume, dissolved in water useful for injection, made up after complete dissolution to 20 liters with water useful for injection and filtered to clear through a glass filter.

The solution obtained was filled into vials of 2 ml volume which were then sterilized at 120° C. for 30 minutes.

EXAMPLE 6

Preparation of suppositories each containing 200 mg of the active ingredient 50 g of colloidal silicon hydroxide were distributed in 2250 g of suppository base, (Adeps solidus) liquefied at 40° to 45° C. An amount of 200 g of 1,6-dimethyl-4-oxo-1,6,7,8,9,9a-hexahydro-4H-pyrido(1,2-a)pyrimidine-3-carboxamide with a 10μ particle size were suspended with little portions of the liquefied suppository base while constant stirring.

The suspension was mixed with the required complementary amount of the liquefied solid fat and filled to a calibrated suppository mould to obtain 1000 suppositories with an average weight of 2.5 g.

EXAMPLE 7

Preparation of a dry syrup containing 100 mg/5 ml of the active ingredient

To a homogenized mixture containing 156 g of sucrose and 240 g of cacao powder, 0.25 g of methyl p-hydroxybenzoate and 0.35 g of propyl-p-hydroxybenzoate as preserving agents and 0.40 g of vanillin as aromatizing agent were added. Thereafter, 20 g of 1,6-dimethyl-4-oxo-1,6,7,8,9,9a-hexahydro-4H-pyrido(1,2-a)pyrimidine-3-carboxamide were weighed to this powder mixture, homogenized again and sieved.

Before use, the mixture was filled up to 1000 g with water.

What we claim is:

1. A method of treating a patient with an existing gastrointestinal ulcer caused by exogenous or endogenous chemical agents, which comprises the step of administering to the patient an effective amount of racemic or optically active 1,6-dimethyl-4-oxo-1,6,7,8,9,9a-hexahydro-4H-pyrido(1,2-a)-pyrimidine-3-carboxamide, in the form of a tablet, dragee, capsule, suppository or injection.

2. The method of treatment defined in claim 1 wherein the gastrointestinal ulcer is a stomach ulcer or an ulcer of the small intestines.

3. The method of treatment defined in claim 1 wherein the gastrointestinal ulcer has been caused by administration of an antiinflammatory agent selected from the group consisting of acetylsalicylic acid, benoxaprofen, fenoprofen, ibuprofen, flufenamic acid, indomethacin, ketoprofen, naproxen, phenylbutazone, piroxicam, and sulindac.

4. The method of treatment defined in claim 1 wherein the gastrointestinal ulcer has been caused by the administration of ethanol.

5. The method of treatment defined in claim 1 wherein the gastrointestinal ulcer has been caused by hydrochloric acid.

* * * * *